United States Patent
Kizilel et al.

(10) Patent No.: US 9,499,715 B2
(45) Date of Patent: Nov. 22, 2016

(54) NANOPARTICLE AND GELATION STABILIZED FUNCTIONAL COMPOSITES OF AN IONIC SALT IN A HYDROPHOBIC POLYMER MATRIX

(71) Applicants: TURKIYE PETROL RAFINERILERI A.S., Kocaeli (TR); KOC UNIVERSITESI, Istanbul (TR)

(72) Inventors: Seda Kizilel, Istanbul (TR); Riza Kizilel, Istanbul (TR); Adem Levend Demirel, Istanbul (TR); Selin Kanyas, Izmir (TR); Derya Aydin, Istanbul (TR); Ramazan Oguz Caniaz, Kocaeli (TR)

(73) Assignees: TURKIYE PETROL RAFINERILERI A.S., Kocaeli (TR); KOC UNIVERSITESI, Istanbul (TR)

( * ) Notice: Subject to any disclaimer, the term of this patent is extended or adjusted under 35 U.S.C. 154(b) by 0 days.

(21) Appl. No.: 15/026,208
(22) PCT Filed: Jun. 24, 2014
(86) PCT No.: PCT/TR2014/000240
§ 371 (c)(1),
(2) Date: Mar. 30, 2016
(87) PCT Pub. No.: WO2015/005883
PCT Pub. Date: Jan. 15, 2015

(65) Prior Publication Data
US 2016/0244630 A1    Aug. 25, 2016

(30) Foreign Application Priority Data
Jun. 26, 2013    (TR) .............................. a 2013/07719

(51) Int. Cl.
*C09D 153/02*    (2006.01)
*C09K 3/18*    (2006.01)
(Continued)

(52) U.S. Cl.
CPC ............... *C09D 153/02* (2013.01); *A61K 9/70* (2013.01); *B01D 61/40* (2013.01);
(Continued)

(58) Field of Classification Search
CPC .... C09D 153/02; C09D 5/00; C09D 7/1208; C09K 3/18; C08L 53/02; B01D 69/148; B01D 61/40; B01D 69/142; B01D 71/027; B01D 71/26; B01D 71/28; C08K 3/36; C08K 5/098
USPC ......................................................... 524/27
See application file for complete search history.

(56) References Cited

U.S. PATENT DOCUMENTS

| 4,973,606 A | 11/1990 | Sterzel et al. |
| 6,943,205 B2 | 9/2005 | Patel et al. |

FOREIGN PATENT DOCUMENTS

| CN | 102382536 A | 3/2012 |
| CN | 102676060 A | 9/2012 |
| WO | WO 2010/017558 A2 | 2/2010 |

OTHER PUBLICATIONS

Written Opinion, pp. 1-7, dated Feb. 12, 2015, received in PCT Application No. PCT/TR2014/000240.
(Continued)

*Primary Examiner* — Susannah Chung
*Assistant Examiner* — Josephine Chang
(74) *Attorney, Agent, or Firm* — Brinks Gilson & Lione

(57) ABSTRACT

A controlled release composite membrane comprising hydrophobic styrene-butadienestyrene block copolymer as hydrophobic continuous medium and hydrophilic functional agents incorporated within silica nanoparticles as hydrophilic dispersed medium and a preparation process of said membrane are described.

4 Claims, 8 Drawing Sheets

(51) Int. Cl.
  *B01D 61/40* (2006.01)
  *B01D 67/00* (2006.01)
  *B01D 71/80* (2006.01)
  *C09D 5/00* (2006.01)
  *C09D 7/12* (2006.01)
  *C08L 53/02* (2006.01)
  *A61K 9/70* (2006.01)
  *B01D 69/14* (2006.01)
  *B01D 71/02* (2006.01)
  *B01D 71/26* (2006.01)
  *B01D 71/28* (2006.01)
  *C08K 3/36* (2006.01)
  *C08K 5/098* (2006.01)

(52) U.S. Cl.
  CPC ........ *B01D 67/0011* (2013.01); *B01D 69/148* (2013.01); *B01D 71/80* (2013.01); *C08L 53/02* (2013.01); *C09D 5/00* (2013.01); *C09D 7/1208* (2013.01); *C09K 3/18* (2013.01); *B01D 69/142* (2013.01); *B01D 71/027* (2013.01); *B01D 71/26* (2013.01); *B01D 71/28* (2013.01); *C08K 3/36* (2013.01); *C08K 5/098* (2013.01)

(56) References Cited

OTHER PUBLICATIONS

International Search Report, pp. 1-4, dated Feb. 12, 2015, received in PCT Application No. PCT/TR2014/000240.
International Preliminary Report on Patentability, dated Nov. 6, 2015, pp. 1-5, received in PCT Application No. PCT/TR2014/000240.
Kanyas et al., "Nanoparticle and Gelation Stabilized Functional Composites of an Ionic Salt in a Hydrophobic Polymer Matrix," PLoS One, 9(2):e88125 (Feb. 2014).
Binks et al., "Macroporous Silica From Solid-Stabilized Emulsion Templates," *Advanced Materials*, 14:24, 1824-1827 (2002).
Imhof and Pine, "Uniform Macroporous Ceramics and Plastics by Emulsion," *Chem. Eng. Technol.*, 21:8, 682-685 (1998).
Imhof & Pine, "Ordered Macroporous Materials by Emulsion Templating," *Nature*, 389, 948-951 (1997).
Wei and Wan, "Hollow Microspheres of Polyaniline Synthesized with an Aniline Emulsion Template," *Advanced Materials*, 14:18, 1314-1317 (2002).

Fig. 1a
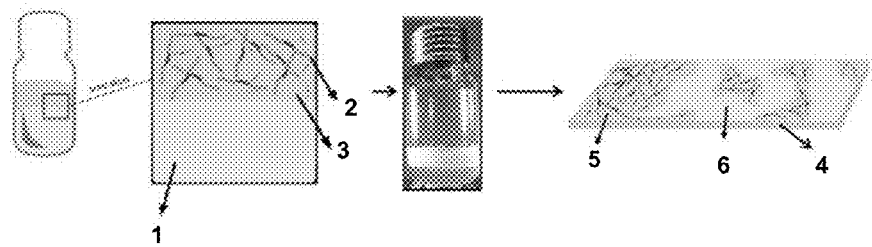
Fig. 1b
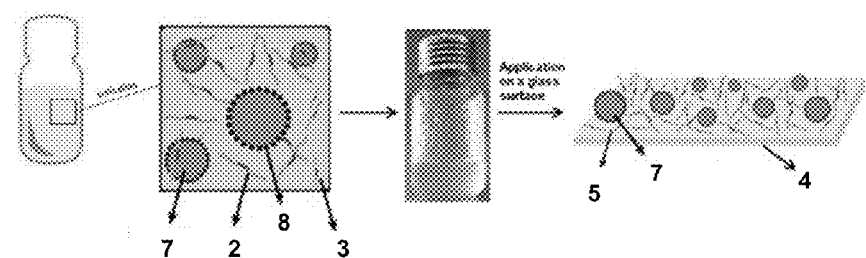
Fig. 2a 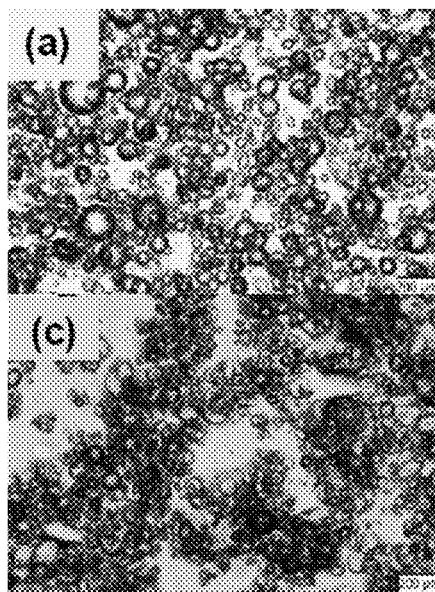 Fig. 2b
Fig. 2c 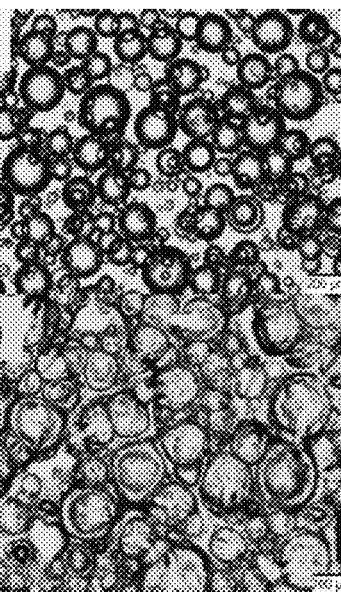 Fig. 2d

NANOPARTICLE AND GELATION STABILIZED FUNCTIONAL COMPOSITES OF AN IONIC SALT IN A HYDROPHOBIC POLYMER MATRIX

RELATED APPLICATIONS

The present patent document is a §371 filing based on of PCT Application No. PCT/TR2014/000240, filed Jun. 24, 2014, which claims priority to Turkey (TR) Application No. 2013/07719, filed Jun. 26, 2013, which are hereby incorporated by reference.

BACKGROUND

Incorporation of hydrophilic functional agents within a hydrophobic matrix has been a conventional challenge in materials science. This challenge can be addressed by forming stable liquid emulsions and using them as templates to form solid-like composites. Emulsions are the mixture of immiscible liquids and spherical dispersed droplets are within a continuous phase. The liquid emulsion droplets need to be robust and have long-term stability, so that the structure of the emulsion droplets throughout the drying process should be maintained. Although micro-emulsions are thermodynamically stable and require little attention for a stabilizing system, emulsion droplets tend to coalesce and phase separate before the templating process, unless caution is taken. It is well established that, as an alternative to surface active molecules, small solid particles attach at fluid/fluid interfaces of two immiscible mediums when the particles are partially wettable by both mediums. This mechanism for use in emulsion templates due to their strong stability is known as "Pickering emulsions".

In a study, Imhof and Pine have templated micro-emulsions of droplet size ranging from 100 to 200 nm (Imhof A, Pine D J (1997) Ordered macroporous materials by emulsion templating. Nature 389: 948-951). They have employed sol-gel processing to cure the continuous phase. The results showed that they were able to make materials with a well: defined pore size difference of, 20%. They have obtained a porous monolith by removal of oil droplets within aqueous continuous medium and gelation of the aqueous medium by sol-gel method (Imhof A, Pine D J (1998) Uniform macroporous ceramics and plastics by emulsion templating. Chemical Engineering & Technology 21: 682-685). In another study, Binks prepared a porous silica monolith by silica particles alone (Binks B P (2002) Macroporous silica from solid-stabilized emulsion templates. Advanced Materials 14: 1824-1827). Such porous monoliths are also proposed to be used as adsorbents, catalytic supports, lightweight structural materials, insulators besides their potential application as filters.

The importance of self-assembly of target materials at the interface to form stable capsules was investigated in a study of Wei and Wan. The authors used polyaniline coated hollow microspheres for self-assembly of aniline monomers around oil-in-water (o/w) droplets in emulsion, and polymerized the shell subsequently. Such capsules are promising to be used as delivery vehicles for controlled-release encapsulation, drug delivery, protection of biologically active agents.

Macroporous systems are proposed to serve mostly as filtering systems, whereas the capsules have been considered to encapsulate either nanoparticles or biomaterials such as drugs, food and cosmetics.

SUMMARY

Described is a controlled released composite membrane comprising a hydrophobic styrene-butadiene-styrene block copolymer as a hydrophobic continuous medium and Pickering emulsion droplets comprising anti-icing agents surrounded and stabilized by hydrophobic silica nanoparticles as a hydrophilic dispersed medium, and a process for the preparation of the composite.

The present disclosure relates to a controlled release composite membrane, as shown, e.g., in FIGS. 1a and 1b, comprising a hydrophobic styrene-butadiene-styrene block copolymer (2) as a hydrophobic continuous medium (5) and Pickering emulsion droplets comprising anti-icing agents surrounded and stabilized by hydrophobic silica nanoparticles (8) as a hydrophilic dispersed medium (6), and a process of preparing the controlled release composite membrane.

The process described here involves incorporation of the anti-icing agents into a hydrophobic styrene-butadiene-styrene (SBS) copolymer as a hydrophobic continuous medium to form a mixture, and stabilization of the mixture with hydrophobic silica nanoparticles using a Pickering emulsion templating method. The resultant colloid system demonstrated enhanced mechanical strength and viscoelastic behavior. Partially hydrophobic silica nanoparticles are used to form Pickering emulsion.

An aspect of described embodiments is to provide controlled release of the active ingredients loaded into the composite of the present invention.

Another aspect of described embodiments is to delay freezing in the surfaces especially asphalt surfaces and in the application of modified bitumen.

Other aspect of described embodiments is to enhance the mechanical properties of polymeric matrix by the homogeneous and stable distribution of anti-icing active and hydrophilic molecules into the SBS-block copolymer which is the most common ingredient of the modified bitumen applications.

BRIEF DESCRIPTION OF THE FIGURES

FIG. 1a. Schematic representation of the preparation process without particle stabilization.

FIG. 1b. Schematic representation of the preparation process with particle stabilization.

FIG. 2a. Optical microscope images of wet emulsions prepared without agar gel in the dispersed phase. Scale bar is 200 μm.

FIG. 2b. Optical microscope images of wet emulsions prepared with agar gel in the dispersed phase. Scale bar is 200 μm.

FIG. 2c. Optical microscope images of dry emulsions prepared without agar gel in the dispersed phase. Scale bar is 200 μm.

FIG. 2d. Optical microscope images of dry emulsions prepared with agar gel in the dispersed phase. Scale bar is 200 μm.

Figure 3A:
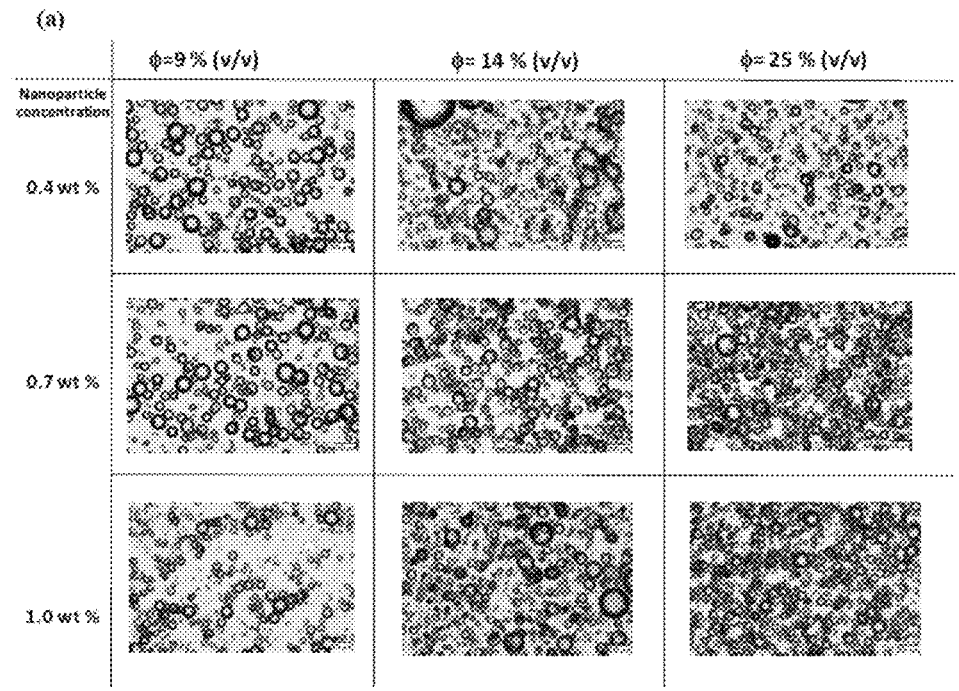
FIG. 3a. Optical microscope images of wet emulsions for altered concentrations of nanoparticles and internal phase volume fractions. Internal phase does not contain agar gel. Scale bar represents 200 μm.

The parts in said figures are individually referenced as following.

An aqueous potassium formate stock solution (1)
SBS block copolymer (2)
Organic solvent (3)
Substrate (4)
Hydrophobic continuous medium (5) comprising SBS block copolymer
Hydrophilic dispersed medium comprising (6) anti-icing agent
Anti-icing agent (7)
Silica nanoparticles (8)

DETAILED DESCRIPTION

In embodiments, as shown, e.g., in FIGS. 1a and 1b, a controlled released composite membrane comprising hydrophobic styrene-butadiene-styrene block copolymer (2) as a hydrophobic continuous medium (5) and Pickering emulsion droplets comprising anti-icing agents surrounded and stabilized by hydrophobic silica nanoparticles (8) as a hydrophilic dispersed medium (6), and the process for the preparation of said composite are disclosed.

The hydrophobic continuous medium (5) comprises a base which is non-polar styrene-butadiene-styrene (SBS) block copolymer (2) and can be compatible with most non-polar surfaces. SBS is the most preferred polymer to modify bitumen.

The hydrophilic dispersed medium (6) comprises Pickering emulsion droplets comprising anti-icing agent surrounded and stabilized by hydrophobic silica nanoparticles (8). The droplets store and induce controlled release of said anti-icing agent. Anti-icing agent (7) may be an ionic salt, preferably potassium formate salt (KCOOH). Ionic salts are widely used agents as for anti-icing and they have very high freezing point depression effect. KCOOH has been preferred as an anti-icing agent (7) over common salts, such as $CaCl_2$, NaCl, or $MgCl_2$, due to its higher freezing point depression effect, low corrosion and, environmentally safe properties. Potassium formate salt is less hazardous than the chloride salts. The advantages of the material prepared according to the methods described include the restricted permeability of the composite structure towards the functional agent, and stability of the template during drying process. It is hypothesized that silica nanoparticles will allow for controlled release of KCOOH through the internal phase domains and through the particle shells.

In order to avoid destructed shapes, to enhance restricted permeability, and to reinforce rheological properties, functional domains can be included in agar gel within the designed material. Pickering emulsion droplets are used as templates for the functional domains, which encapsulate the anti-icing agent (7) in the functional membrane coating.

The composite is suitable for any application in which hydrophilic functional agents should be homogeneously dispersed and controllably released, such as anti-icing agents for surfaces, biomolecules or drugs for therapeutic applications, etc., and said composites can be used in several areas like enhancing the mechanical properties of the surfaces, e.g., asphalt by the controlled release of the molecules reducing the freezing point of the water, and biological applications as controlled drug carrier for therapeutic purposes.

The described process comprises incorporation of anti-icing agents into a hydrophobic styrene-butadiene-styrene (SBS) copolymer (2) and stabilization of the mixture with hydrophobic silica nanoparticles (8) using the Pickering emulsion templating method.

The particle stabilization to design a functional composite includes the use of an anti-icing agent with hydrophobic silica nanoparticles (8).

The resultant colloid system demonstrated enhanced mechanical strength and viscoelastic behavior. Partially hydrophobic silica nanoparticles are used to form Pickering emulsion.

The process for the preparation of the composite with particle stabilization comprises the following the steps:
1. Hydrophobic silica nanoparticles are dispersed in an organic solvent (3), preferably cyclohexane,
2. SBS polymer is dissolved in cyclohexane to form hydrophobic continuous medium,
3. Aqueous anti-icing agent solution is suspended in said hydrophobic continuous medium,
4. Pickering emulsion is formed, and
5. Said emulsion is applied on a glass surface to form a solid layer.

Primary particle size of hydrophobic fumed silica nanoparticles (8) is 10-15 nm; preferably 12 nm. Hydrophobic silica nanoparticles (8) are used as stabilizing agent. Nanoparticle use is necessary to prepare a stable solution. If it is not used, the anti-icing agent is not dispersed homogenously. Other nanoparticles that may be used include, preferably, particles having both hydrophobic and hydrophilic groups thereon.

Different from previous studies on emulsion templating, which either obtained a porous monolith or isolated capsules, functional domains with or without gel phase embedded on a monolith membrane has been prepared, and characterized here. The domains can serve as functional capsules which store anti-icing agents and are surrounded by nanoparticles. Thus, utilizing solid particle stabilized droplets, gelation of the functional phase and loading hydrophilic agents within the membrane impart novelty to potential applications for similar research areas.

The described composite is promising for future applications, such as monolith scaffolds in tissue engineering, platforms for drug delivery from a surface, tool for food processing or coating for delivery of functional anti-icing materials. This encapsulation method is not only applicable to storing anti-icing agents but it is extended to any water soluble material. A variety of materials including optically and chemically active materials can be incorporated into the composite and the described composite can find use in applications where functional materials other than ionic salts are incorporated into hydrophobic monoliths.

Said template emulsion is designed to serve both as a dry membrane and a viscous stable multiphase system to be integrated into other hydrophobic mediums that would otherwise be incompatible with the delivery material. In order to manipulate the affinity towards various other mediums, hydrophobic polymers other than SBS can be favored.

Exemplary embodiments and the experiments are provided below.

Following composites are prepared:

- Wet/Dry emulsions without agar gel in the dispersed phase.
- Wet/Dry emulsions with agar gel in the dispersed phase.
- Emulsions prepared without agar gel in the dispersed phase.
- Wet/Dry emulsions prepared with agar gel in the dispersed phase.

Preparation of Silica Nanoparticle and SBS Solutions.

Silica AEROSIL 8160 nanoparticles were dispersed in cyclohexane with three different concentrations: 0.4, 0.7, and 1.0 gram in 100 mL cyclohexane. The dispersion was carried out by high energy application via ultra-sonication tip (73 MS, 50% amplitude, 50 Hz frequency) for 3 minutes. Ice bath was applied every 45 seconds to avoid excessive temperature rises. During the period between nanoparticle dispersion and emulsion preparation, the nanoparticle suspension was kept in ultrasonic bath in order to avoid agglomerations that may arise from steady positioning. Dynamic Light Scattering (DLS) measurements indicated that agglomeration could not be fully avoided. Nanoparticle dispersions of all concentrations outturned particle sizes of the range 100-150 nm.

The SBS stock solution was prepared by mixing 110 mg/ml SBS in cyclohexane. The mixture was stirred on magnetic stirrer at room temperature.

Preparation of the Emulsion without Gelation of the Internal Phase.

The moisture in the solid KCOOH was eliminated through freeze-drying. An aqueous KCOOH stock solution (0.5 g/mL) (1) was prepared by dissolving the salt in distilled water at room temperature. In order to obtain emulsion templates with just aqueous KCOOH solution in the dispersed phase, 0.5 mL of nanoparticle stock solution was added into aqueous KCOOH solution in the amounts of 0.5, 0.25, or 0.15 mL to obtain emulsions with 9, 14, or 25% (v/v) internal phase fractions, respectively. To this solution 1 mL of SBS stock solution was added to obtain emulsions with SBS in the continuous phase. The stability of the emulsions in vials was observed for 3 days at room temperature. For parametric sensitivity experiments, emulsion solutions containing altered concentrations of nanoparticles and internal phase volume fraction were examined. Table 1 demonstrates the concentrations of the emulsions prepared to investigate the effects on the properties of emulsion templates. Internal phase volume fraction was calculated with respect to the emulsion total volume (water+particles+SBS solution).

TABLE 1

| Oil | Internal Volume Fraction % (v/v) | Silica nanoparticle concentration in stock solution % (w/v) |
|---|---|---|
| SBS Solution | 9 | 0.4 |
| SBS Solution | 14 | 0.7 |
| SBS Solution | 25 | 1.0 |

Preparation of the Emulsion with Gelation of the Internal Phase.

Agar solution was prepared by adding 1% (w/w) agar powder in distilled water. The mixture was cooked in microwave oven until it boiled and all powder was dissolved. Subsequently 0.5 g of KCOOH was dissolved in 1 mL of agar solution, which yielded 0.5 g/ml KCOOH (s) salt solution in agar. Three different fractions of internal volume of salty agar solution were added into three different concentrations of nanoparticle-cyclohexane dispersion. The particle dispersion was kept at room temperature. Stock nanoparticle solution concentrations of 0.4% (w/v), 0.7% (w/v), 1.0% (w/v), and internal volume fractions of 9 (v/v), 14% (v/v), 25% (v/v) were prepared. For example, for an internal volume fraction of 25% (v/v), 0.5 mL of the KCOOH agar solution was added into 0.5 mL of nanoparticle stock solution phase under high shear applied by vortex at maximum speed for 5 seconds. As hot agar solution was mixed in the cyclohexane, the aqueous solution formed well-dispersed droplets which were stabilized by nanoparticles. The stabilized agar droplets instantly cooled as they mixed with the nanoparticle solution at room temperature. As agar solution turned into gel phase, hydrophilic gel droplets that were dispersed in cyclohexane formed an emulsion. Actually, 1 ml of the concentrated SBS polymer in cyclohexane (110 mg/ml) was added drop-wise into 1 mL of the KCOOH, agar, and nanoparticle solution with gentle mixing.

Casting of Emulsions on Substrate Surfaces.

Obtained emulsions were applied on substrate surfaces to dry them. Microscope glass slides were rinsed with ethanol and distilled water. The substrates were dried with nitrogen and 100 µl of each emulsion solution was deposited on glass slides separately. The cast membranes on glass slides were dried at 15° C. The membranes were considered to be dry when the solvent evaporated from both phases of the emulsion, and membranes appeared elastic.

Here, neither the continuous nor the dispersed phase of the emulsion was removed. Instead, they were strongly stabilized to compose aqueous delivery capsules embedded in a hydrophobic polymer monolith membrane. The droplets were functionalized by loading with aqueous KCOOH as a representative hydrophilic agent. The emulsion was stabilized by solid particle stabilization method, utilizing surface modified partially hydrophobic silica nanoparticles. The functionalized packages with gel domains were also fabricated and compared to the ones without gel domains. The effect of parameters such as gelation, nanoparticle concentration and dispersed phase volume fraction on the stability of the initial emulsion, the rheology of the partially dried viscous emulsion, and on the hydrophobicity and morphology of the resultant membrane were investigated in detail.

Stable emulsions have been prepared with the two immiscible phases; where hydrophilic liquid droplets are dispersed in a polymer solution medium (FIGS. 1*a* and 1*b*). Next, emulsions templates were formed from the dispersed droplets of the initial emulsion. The method involves an elastic membrane platform based on the continuous polymer phase; and functional domains, where domains are spread on a solid platform at a macroscopically homogeneous order (FIG. 1b). Emulsion stabilization prior to drying offers the possibility to integrate two opposite surface properties in a resultant elastic membrane.

Optical microscope images prepared with internal volume fraction $\phi=0.33$, and nanoparticle concentration of 0.7% (w/w) are shown in FIGS. 2a through 2d. FIGS. 2a and 2b display the differences resulted from the presence of gel phase in the wet emulsion droplets, which contained aqueous KCOOH, right after being placed on the glass slide. The aqueous gel droplets were larger and much more predominantly shaped than the ones without gel. Furthermore, the droplets without gel had a tendency to merge and lose stability by forfeiting their spherical shapes, especially when particle concentration was low (0.7% wt of particles). It can be observed from FIG. 2b that gelation of the internal phase with the use of agar contributed greatly to homogeneity of the dispersed phase.

The effect of gelation of the internal phase in the wet state of the emulsion could also be observed in dry states of the membrane templates. As can be observed in FIG. 2c, the domains without gel phase could not retain the original spherical shapes upon drying. The gel domains on the other hand, preserved their three dimensional size and morphology to a large extent, despite having been slightly distorted due to volume changes of the continuous phase during drying (FIG. 2d). Furthermore, the gel cores within the domains protected the gel droplets from cracking. They remained resistant against the capillary pressure effects, which occurred during evaporation of the solvent in both phases. The elimination of cracks allows for better protection of the anti-icing agent, which was incorporated within capsules. A crack-free shell around the functional domains is highly desirable, as this would contribute to the stability of the membrane composite as a whole, which may further allow for better controlled release profiles of the functional agent from the gel domains towards their surroundings. Additional observation that could be made about FIGS. 2a through 2d is that emulsions that were prepared with agar gel in the internal phase have larger droplet sizes compared to the emulsions prepared with only functional aqueous solution.

Figure 3B:
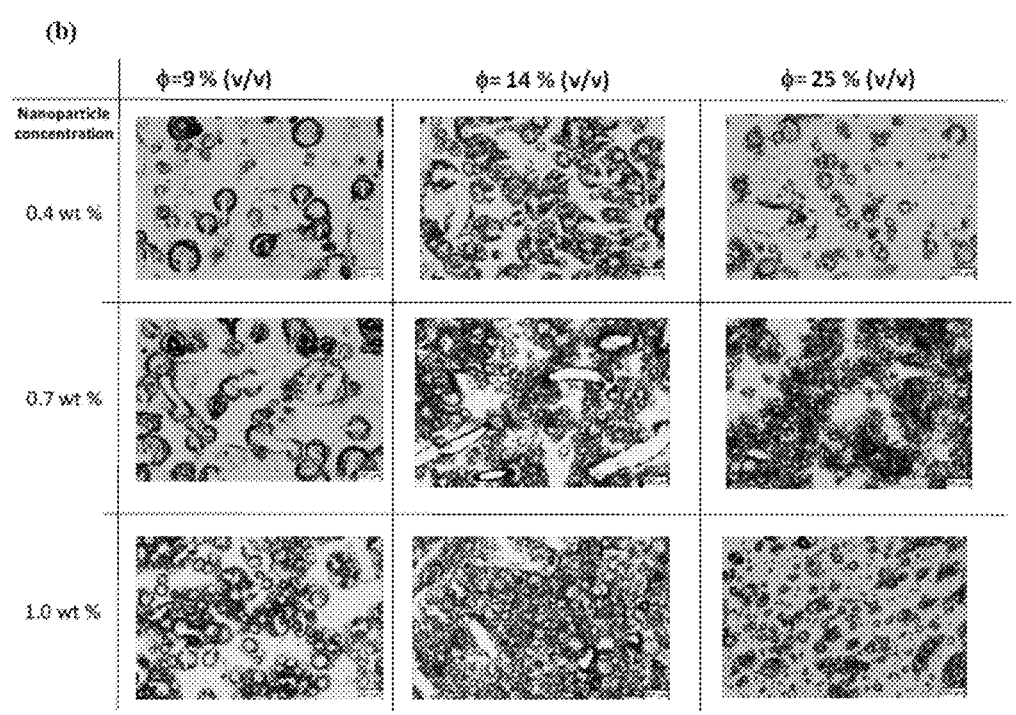
FIG. 3b. Optical microscope images of dry emulsions for altered concentrations of nanoparticles and internal phase volume fractions. Internal phase does not contain agar gel. Scale bar represents 200 μm.
Figure 9A:
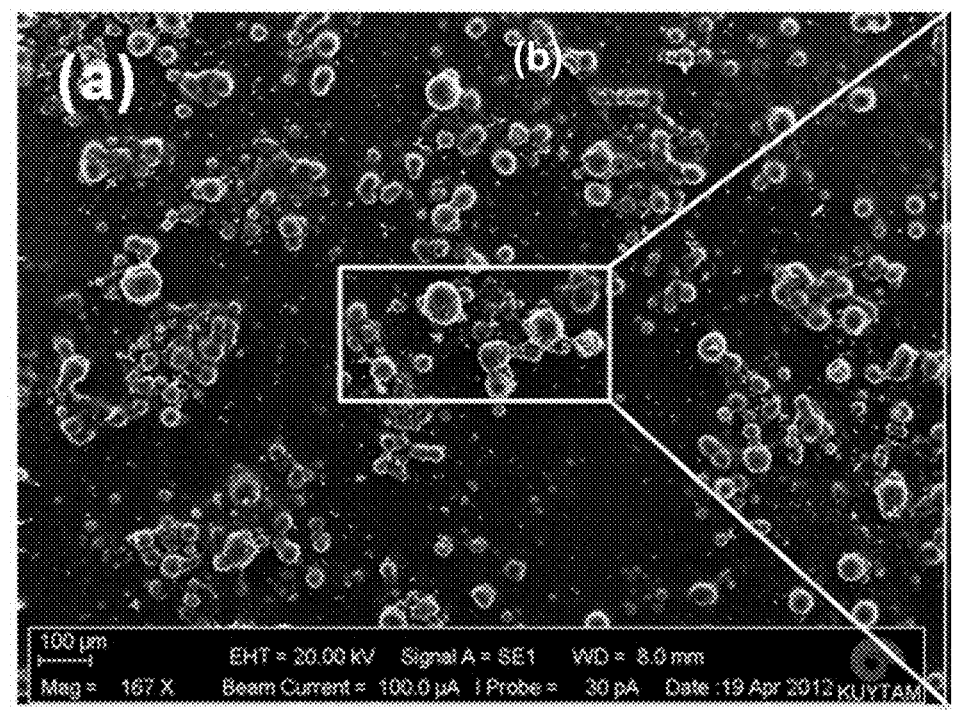
FIG. 9a. Scanning electron microscope image for the templated dry emulsion with gel cores.
Figure 9B:
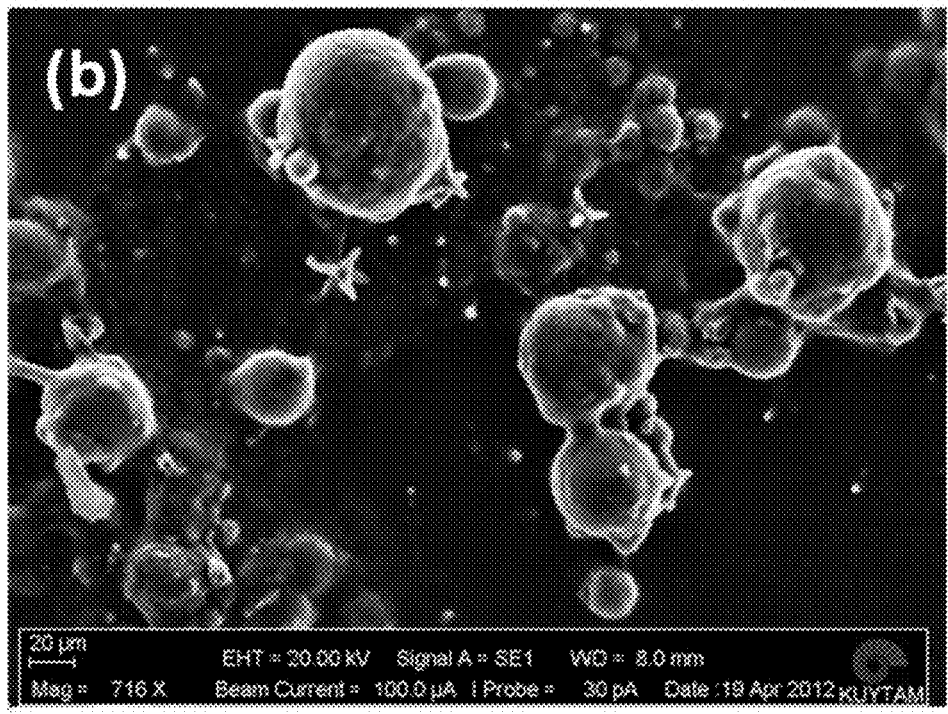
FIG. 9b. Closer view of the scanning electron microscope image for the templated dry emulsion with gel cores.

Effect of Particle Concentration and Internal Phase Volume Fraction on Average Wet/Dry Droplet Size In order to investigate the effect of critical parameters on the properties of wet and dry emulsions, samples were prepared with different internal volume fraction and particle concentration conditions. Emulsion samples were placed on glass slides separately, and were observed under the microscope (Nikon, Eclipse Ni-U) in both wet and dry states (FIGS. 3a and 3b). Optical micrographs were obtained by placing emulsion samples on previously cut square shaped glass slides. They were then placed in an optical microscope attached to a DS camera control unit (Model: DS-L3) both before (wet) or after solvent evaporation (dry). The surface images were imported to a software program (Kameram) for analysis of the droplet sizes and morphologies. Morphologies of both wet and dry castings were found to be dependent on the constituents of the dispersed phase. The effects of particle concentration in the emulsion, internal phase volume fraction, and gelation of the internal phase on the morphology of membranes have been studied (Table 1). The morphology of an emulsion sample that contains agar gel in the internal phase was analyzed via Scanning electron microscope (Zeiss Ultra Plus, Bruker; Optronik Ltd Sti, Ankara, Turkey) (FIGS. 9a and 9b).

The effects of the internal phase volume fraction and nanoparticle concentration on average droplet size have been demonstrated in FIGS. 3a and 3b for altered concentrations of nanoparticles and internal phase volume fractions. Internal phase does not contain agar gel. For the case of emulsions prepared with the functional aqueous solution, the average size of the wet droplets or the dry domains show similar dependencies on particle concentration and internal phase volume fraction. The smaller average diameter of the dry samples is simply due to the shrinkage phenomenon which occurs during evaporation of the solvent. FIG. 3b demonstrates that emulsion templates have distorted structures and lose their morphology upon drying. Independent from nanoparticle concentration or internal volume fraction, cracking of droplets during solvent evaporation resulted in the formation of irregular domains.

Figure 7A:
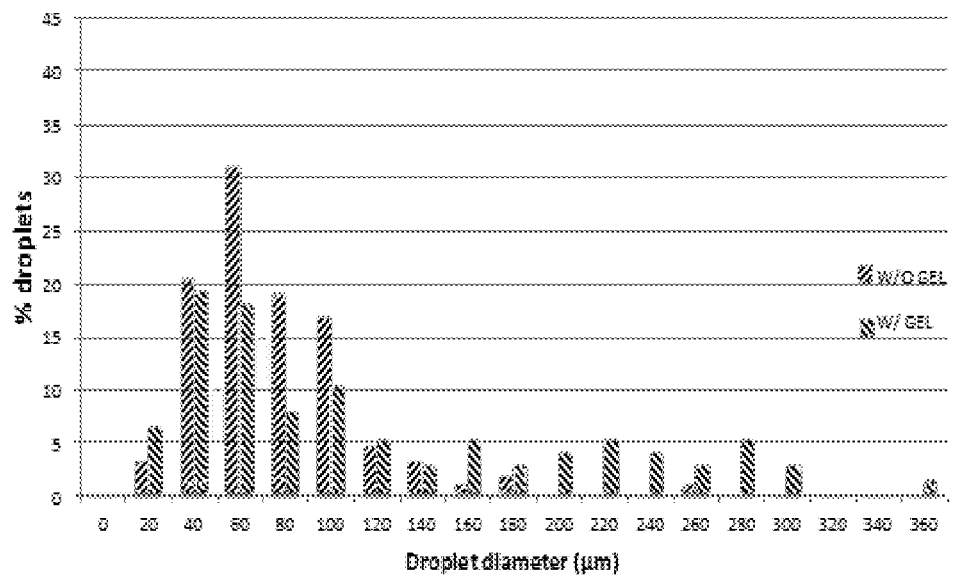
FIG. 7a. Droplet size distribution for emulsions when internal phase volume fraction (φ) of 0.17, and nanoparticle concentration of 1.0% (w/w) were used.
Figure 7B:
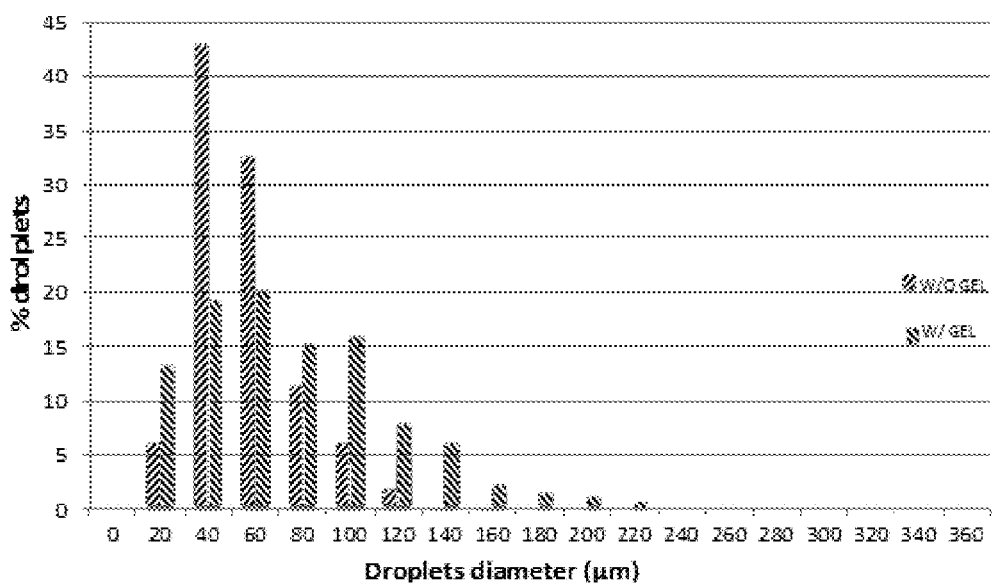
FIG. 7b. Droplet size distribution for emulsions when internal phase volume fraction (φ) of 0.33, and nanoparticle concentration of 1.0% (w/w) were used.

Increasing the internal phase volume caused smaller sized droplets and smaller dry domains (FIGS. 7a and 7b). In FIG. 7a, average droplet size was measured as 120.65 µm, when gelation occurs within the internal phase. Average droplet size was measured as 74.89 µm in the absence of gelation. In FIG. 7b, average droplet size was measured as 74.3 µm, when gelation occurs within the internal phase. Average droplet size was measured as 55.13 µm in the absence of gelation.

Figure 4A:
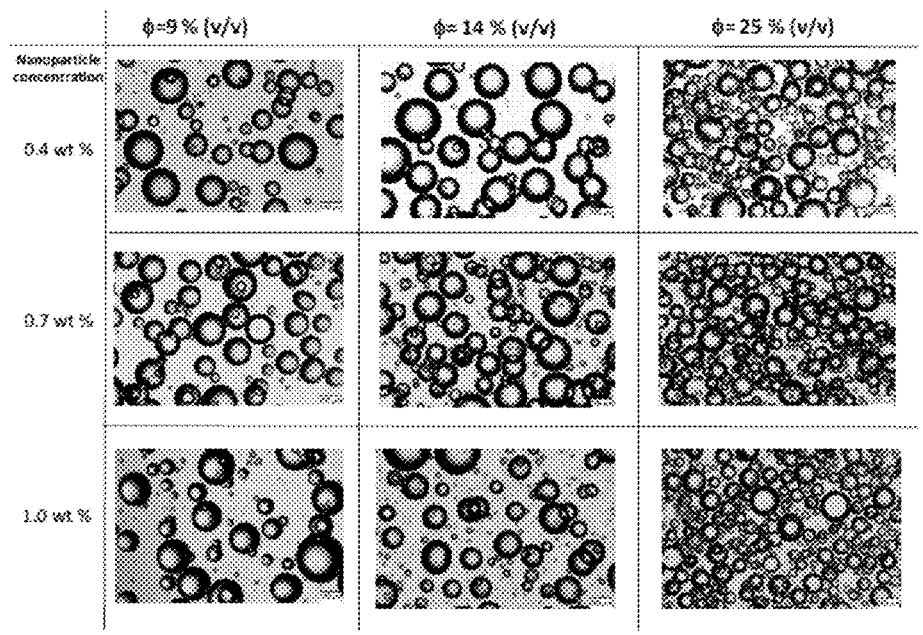
FIG. 4a. Optical microscope images of wet emulsions for altered concentrations of nanoparticles and internal phase volume fractions. Internal phase contains agar gel.
Figure 4B:
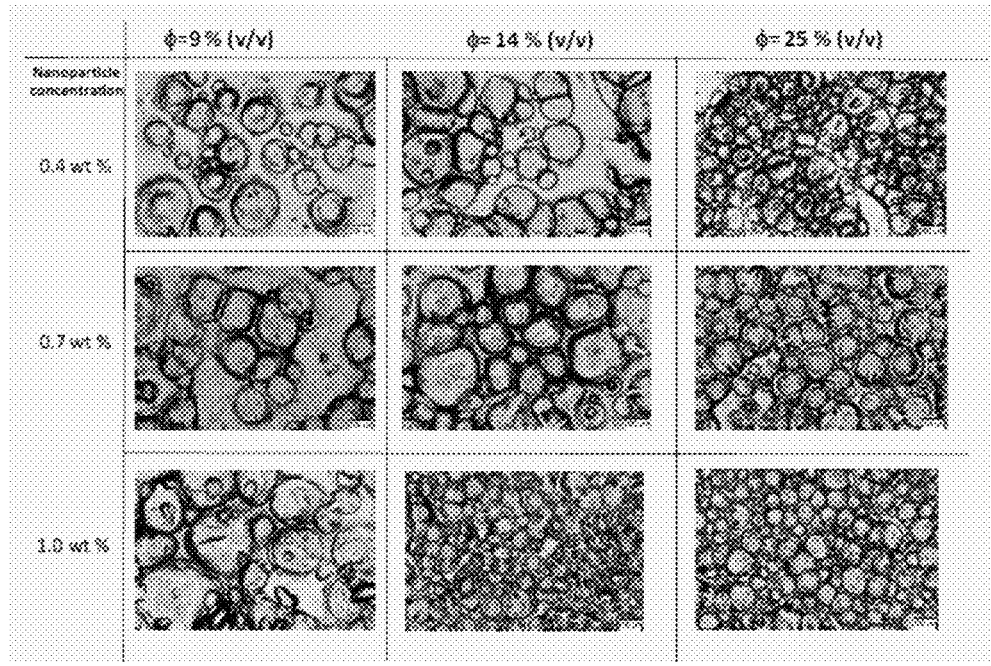
FIG. 4b. Optical microscope images of dry emulsions for altered concentrations of nanoparticles and internal phase volume fractions. Internal phase contains agar gel.

FIGS. 4a and 4b demonstrate the effect of particle concentration and internal phase volume fraction on the morphology of both wet and dry states of the emulsions prepared with agar in the aqueous phase. The figures indicates that the droplets for both wet and dry states were larger in size compared to the emulsions prepared with only functional aqueous solution in the internal phase. Lower particle concentration was inadequate to stabilize all the internal phase in the shape of spherical droplets. However, for lower internal volume ratios, the samples with agar in the internal phase deviated from the behavior of non-gelled ones. Due to the intrinsic stiffness of the gel droplets, 0.7 and 1.0% (w/v) particle concentrations were sufficient to stabilize high amount of internal phase into spherical forms. For the emulsions prepared with gelation in the internal phase, increases in nanoparticles concentration in the stock solution resulted in smaller droplet sizes. Also, low internal phase fraction induces smaller total surface area for droplets. Thus, larger droplets form to allow for the complete particle coverage of droplets.

Figure 6A:
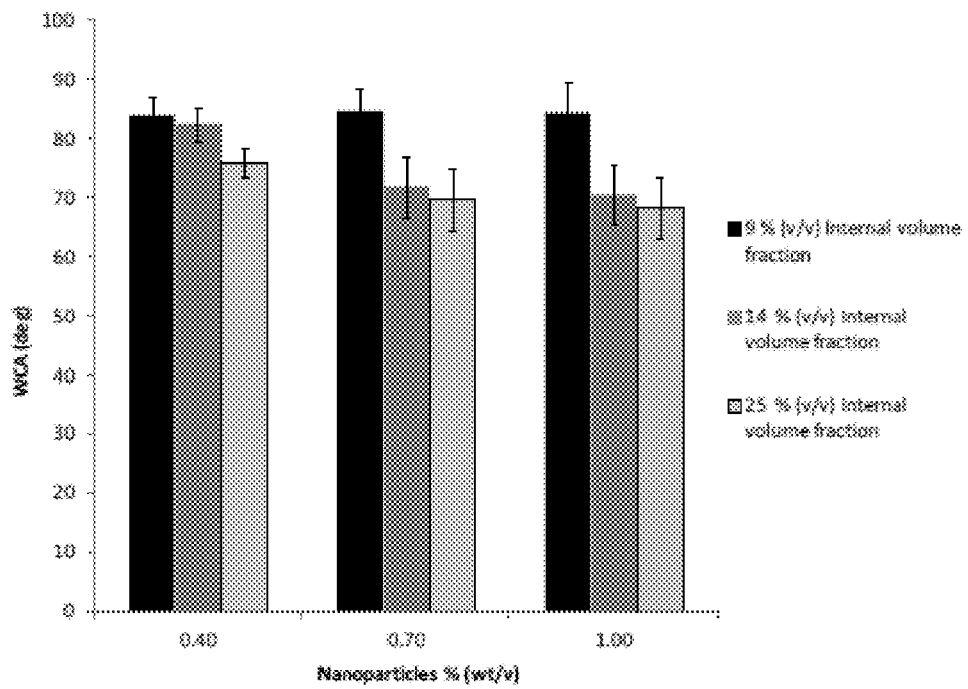
FIG. 6a. Water contact angle (WCA) immediate measurements after deposition of water droplets on the surface.
Figure 6B:
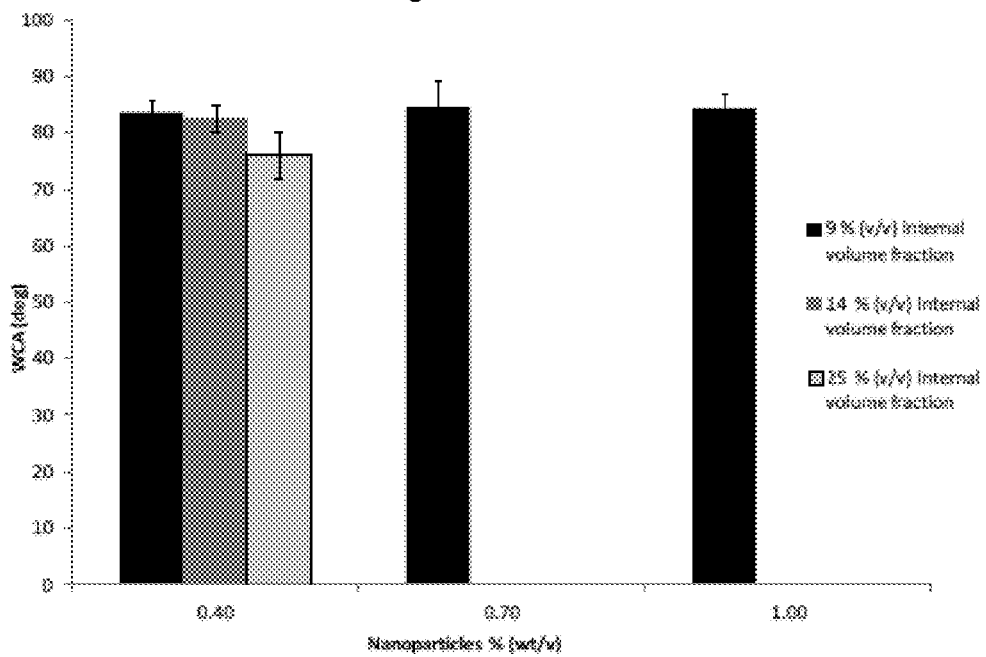
FIG. 6b. Water contact angle (WCA) measurements after 15 seconds of the deposition of water droplets on the surface.

FIGS. 6a and 6b show water contact angle (WCA) measurements on functional membranes with gelation of internal phase. Each series represents an internal volume fraction as displayed in the legend. Horizontal axis represents particle concentration in (w/w). FIG. 6a displays the distribution of droplet size for wet emulsions formed with 17% (v/v) internal volume fraction and 1.0% (w/v) nanoparticle concentration. It was observed from the figure that gel domains were distributed along a wide range of droplet size, starting from 20 µm and extending up until 300 µm diameter. The droplets without gel occupy a narrower size range of 20-180 µm. The figure also demonstrates that, gelation of the dispersed phase promoted the formation of droplets around 20 µm, where the number of droplets with gel phase that were bigger than 180 µm diameter was more in number than the droplets without gel phase. For the case of no gel in the dispersed phase, the greatest size that a non-gel droplet could reach was 180 µm. The average droplet sizes calculated also agree with this observation, and showed that the droplets with gel tended to maintain greater sizes, despite the fact that small gel droplets were possible (Table 2). Table 2 shows average droplet/domain sizes (µm)

for all samples in wet and dry states with respect to internal volume fraction (horizontal) and particle concentration % (vertical). FIG. 6b demonstrates the distribution of droplet size for wet emulsions formed with 25% (v/v) internal volume fraction and 1.0% (w/v) nanoparticle concentration. Similar trends were obtained, where the maximum diameter of a droplet without gel phase was 160 μm, while gel droplet sizes were spread on a wider range, reaching a droplet diameter of 220 μm. Minimum diameter for both droplets with or without gel were about 20 μm.

TABLE 2

| | WET | | | DRY | | |
|---|---|---|---|---|---|---|
| Internal volume fraction (% (v/v)) | 9 | 14 | 25 | 9 | 14 | 25 |
| Nanoparticle concentration % wt | Without gelation in the internal phase | | | | | |
| 0.4% | 95.25 | 78.82 | 49.73 | 91.24 | 78.43 | 41.27 |
| 0.7% | 151.11 | 120.18 | 101.67 | 120.98 | 112.43 | 96.37 |
| 1.0% | 101.65 | 74.89 | 55.06 | 95.17 | 73.32 | 49.03 |
| Nanoparticle concentration % wt | With gelation in the internal phase | | | | | |
| 0.4% | 248.12 | 160.26 | 101.24 | 240.67 | 158.65 | 102.38 |
| 0.7% | 208.03 | 162.14 | 122.25 | 175.98 | 166.91 | 89.59 |
| 1.0% | 196.09 | 120.65 | 74.24 | 175.43 | 119.07 | 73.89 |

Contact Angle Measurements.

Water contact angles (WCA) on surfaces of dry cast membranes were determined at room temperature and ambient relative humidity using goniometer (DataPhysics instruments, Germany). The membrane surfaces were 0.5-1 cm² wide. The membranes were characterized after solvent evaporation. A water droplet of 5 μl was deposited on the surface of each dry membrane and advancing contact angles were measured. All of the values reported are the average of four measurements taken at different locations of an individual membrane and have a maximum error of ±4°.

FIG. 4a shows that low internal phase volume fraction (9% (v/v)) along with reduced particle concentration leads to the formation of giant (200-400 μm) functional domains. This occurred as a result of energy favor of full coverage of droplets in the emulsion. The particles in the system tend to minimize the interfacial area between the continuous polymer phase and the aqueous gel phase. However, full coverage requires reduction in the surface area of functional droplets, thus increase in their size. The supportive gel structure further contributed to the enlargement of emulsion droplets. As particle concentration increased, greater interfacial area, accompanied by smaller droplet size and greater number of droplets per unit area were obtained (FIGS. 4a and 4b). This effect of particle concentration on droplet size has also been reflected on the templated dry membranes (FIG. 4b). The giant droplets surrounded by the particles from 0.4 (w/v) suspension yielded similarly large dry domains (FIG. 4b). It should also be noted that increasing internal volume phase fraction resulted in an increased contact of droplets in wet state and dry state. When the internal phase volume fraction was high, continuous phase SBS polymer base was completely occupied by functional domains. Thus, more internal phase yielded small and compact domains that are slightly deformed upon drying due to pressing on each other (FIG. 4b).

These observations related to the decrease in droplet size with an increase in internal phase volume fraction or increases in nanoparticle solution concentration are also consistent with the previous findings. For example, Akartuna et al. found that increasing the concentration of poly (vinylidene difluoride) (PVDF) particles lead to a decrease in droplet size of wet emulsions prepared with water-in-oil emulsions. This was due to the higher viscosity of the original nanoparticle solution, which caused higher shear stress on the aqueous phase droplets during mixing. Similarly, increasing water content in the emulsions at a fixed particle concentration decreased droplet size. The reason for this effect was explained by increased viscosity of the emulsion with high water content, which resulted in random close packing for the droplets.

The emulsions prepared in this study with agar gel in the internal phase, have been observed to have defined spherical shapes of dispersed droplets. This may suggest enhanced stability of the emulsions with agar gel in the internal phase. Gelation of the internal phase resulted in the formation of highly dense and stiff droplets within the emulsions, which influenced both the size and the shape of the functional domains. The intended function of nanoparticles for the emulsion templates prepared in this study has primarily been the stabilization of the emulsions for a long period of time such that homogeneously distributed functional domains in the final membrane could be obtained. The stabilization effect of particles was better distinguished in the samples where agar gel was not present in the internal phase, since gel cores remained stable at all nanoparticle concentrations used. In the samples prepared with agar gel, the spherical shapes of the emulsion droplets and templated domains were preserved in the wet state, regardless of the nanoparticle concentration used. The gel domains do not sustain the droplets perfect spherical shapes in dry state; however, they remained stiff enough to maintain a three dimensional closed shape (FIGS. 4a and 4b). In addition to the contribution to stability of emulsions, nanoparticles have effects on gel droplet size and on the bridging behavior between stable droplets. Dry domains were slightly smaller but comparable in size to their initial wet droplet phase.

Measurement of the Viscosities of the Emulsions

Rheological measurements were performed at 25° C. using a stress-strain controlling rheometer. (Discovery Hybrid Series-2) from Thermal Analysis (TA) Instruments with a profiled parallel-plate geometry (20 mm plate diameter). Experiments were carried out with a mechanically set gap of 950 μm. Flow tests were conducted to determine viscosities of the wet emulsions by gradually increasing the shear rate from 0.01 to 100 1/s. Oscillatory tests were conducted to measure G' and G" (storage and loss moduli) of the wet emulsions by frequency sweep from 1 to 100 Hz with a strain set at 0.2%.

Figure 5A:
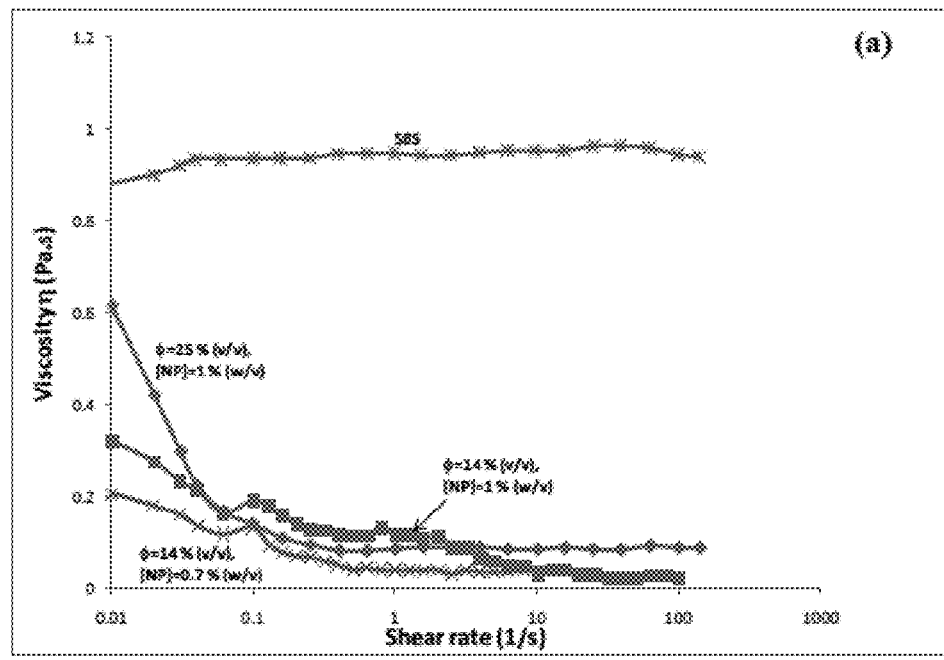
FIG. 5a. Viscosity versus shear rate profiles for emulsions with no gelation of the internal phase.
Figure 5B:
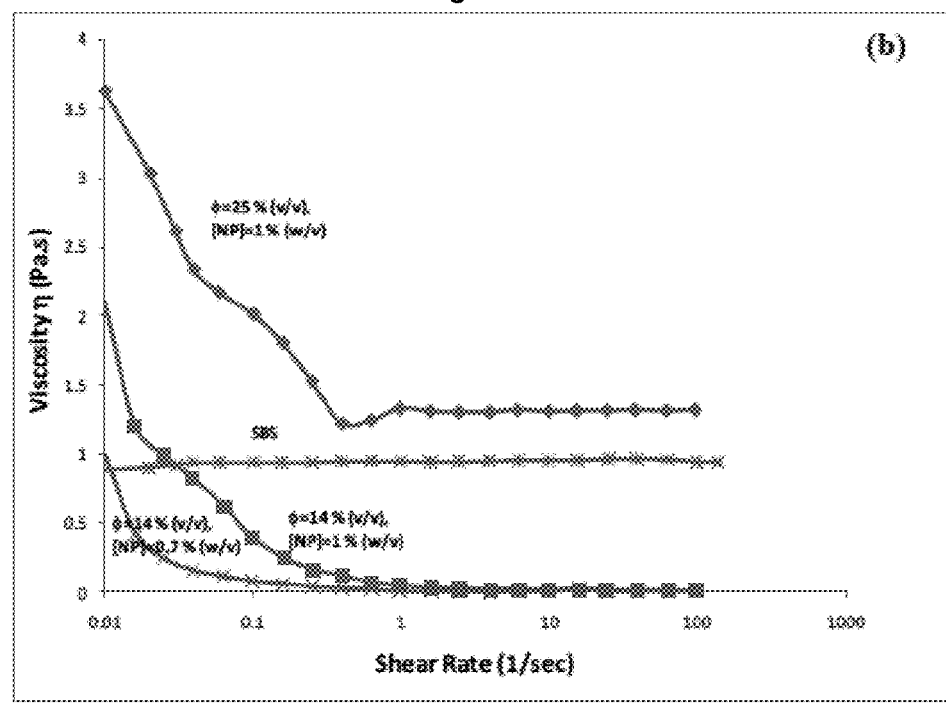
FIG. 5b. Viscosity versus shear rate profiles for emulsions with gelation of the internal phase.

For these samples, viscosities were compared with the viscosities of emulsions prepared without agar in the internal phase. In FIG. 5a and FIG. 5b, viscosity versus shear rate profiles for homogeneous SBS solution have been included for comparison. It is observed from FIG. 5a that emulsification within SBS solution without agar gel in the internal phase induced decreases in viscosities compared to the homogeneous SBS dissolved in cyclohexane. It should be noted that SBS solution used for this measurement has the same concentration as the continuous polymer phase of the emulsions prepared with aqueous solution and is equal to 73 mg/ml. SBS solution shows Newtonian behavior, emulsions show shear thinning which is an indication of "structuring" at zero-shear and structure breakage at larger shear. This result could be explained by the disturbed continuity within the whole fluid, and formation of a structure with the addition of aqueous phase. This weakening of viscosity was improved with increasing the nanoparticle stock solution concentration, increasing the internal phase, or with gelation of the internal phase (FIG. 5a). FIG. 5b demonstrates that the emulsions prepared with 25% (v/v) dispersed phase with agar and 1% (w/v) nanoparticle concentration, had higher viscosities compared to the SBS solution alone. The emulsions prepared with agar gel in the internal phase had higher viscosities than the emulsions that had liquid aqueous droplets in the internal phase only. The addition of higher nanoparticle concentration or increasing internal volume fraction promoted viscosities of the samples prepared with or without gel in the internal phase.

The fact that particle addition enhances viscosity is supported by previous studies.[29] The stability of the emulsions was promoted with increased nanoparticle concentration, which increased resistance to flow. As a result more stable droplets within emulsion yielded higher viscosities. Higher number of particles also caused smaller droplets with greater quantity. The droplet size d is proportional to the $\sigma/\eta\gamma$ where $\sigma$ is the interfacial tension; $\eta$ is the viscosity of emulsion, and $\gamma$ is the applied shear rate. Based on the relation where $d \sim \sigma/\eta\gamma$, the smaller average droplet sizes of emulsions prepared from suspensions with increased solids content are expected to have higher viscosities ($\eta$). Increased droplet surface area by reduced droplet size means that interfacial friction among droplet surfaces will be promoted, which in turn enhances viscosity. In addition, spatial hindrance caused by higher number of droplets per unit volume causes an increase in viscosity.

FIGS. 5a and 5b display increased viscosities for emulsions prepared with or without gel in the dispersed phase. The figure indicates that higher viscosities were observed for the samples containing higher amount of aqueous internal phase. This can be explained by increase in the total surface area with reduced droplet size reduction, as well as the spatial hindrance caused by the higher amount of internal phase ($\phi$) within the emulsion. The collusions among droplets increase, when the total volume occupied by the droplets in an emulsion is high. The additional friction and collusions which $\phi$ increase brings along causes an enhancement in viscosity. In addition, all emulsions, consisting of gel or aqueous dispersed phase demonstrated shear thinning behavior (FIGS. 5a and 5b). Sole SBS solution on the other hand, showed a linear trend for viscosity with respect to shear stress. The change in rheological behavior upon emulsification can be attributed to the discontinuity which the droplets create within the undisturbed continuous polymer medium. Emulsion samples with the two internal volume fractions ($\phi$) and two nanoparticle concentrations demonstrated shear thinning behavior. The shear thinning behavior rate was more pronounced in the emulsions with gelation in the internal phase compared to the case where there was no gelation in the internal phase. As shear rate increases, hydrodynamic forces become large enough for droplet flocs to deform, elongate, and align with the shear field. Eventually they get disrupted and this leads to a rapid decrease in viscosity. In addition, continuous phase, which is trapped between flocs, can be released and this further lowers the viscosity.

Figure 8A:
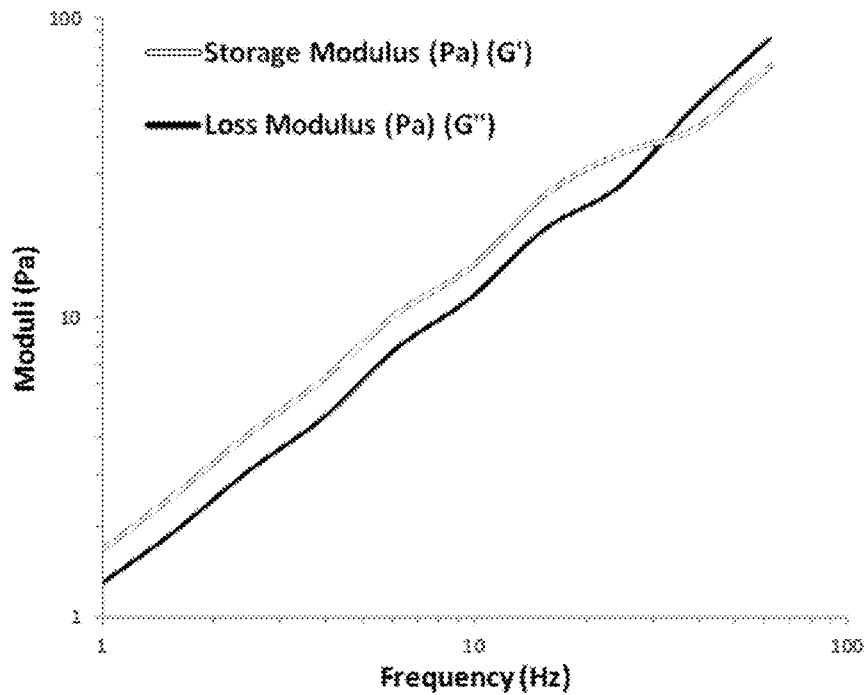
FIG. 8a. Loss and storage moduli in response to frequency for the template emulsion of gel cores (φ)=0.17, 0.7% wt. particle concentration and 0.17 internal phase fraction).
Figure 8B:
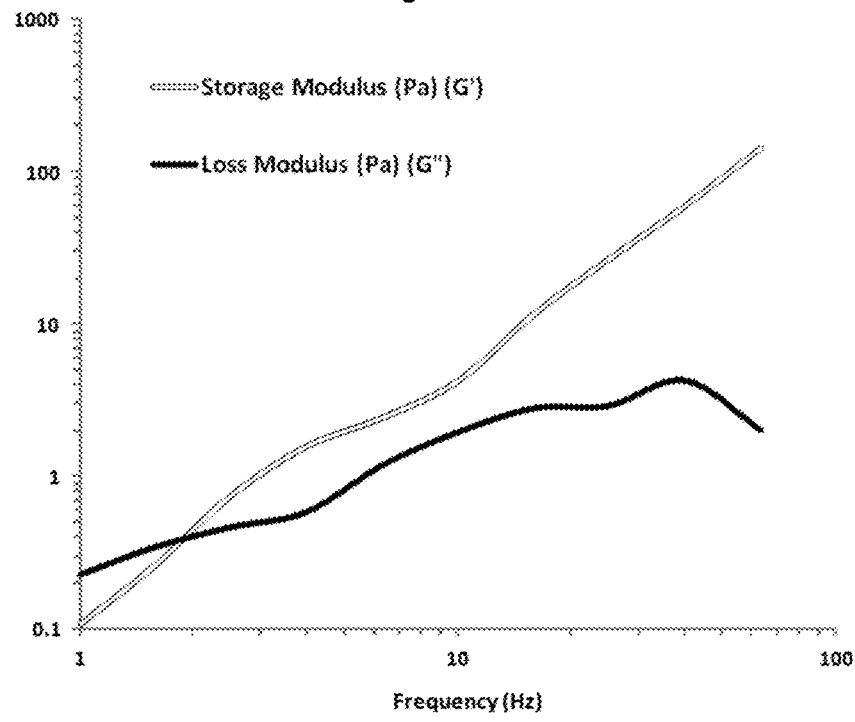
FIG. 8b. Loss and storage moduli in response to frequency for the template emulsion of non-gel cores (0.7% wt. particle concentration and 0.17 internal phase fraction).

Storage modulus (G') and loss modulus (G") of emulsion samples with or without gelation in the internal medium were investigated under oscillatory testing with altered frequency. At low frequencies below 2 Hz, the loss moduli were greater than the storage moduli for both emulsions with or without gelation in the internal medium (FIGS. 8a and 8b). At a specific point during frequency increase, G' exceeds G", which indicates solid-like behavior beyond that frequency. For the emulsions that contain agar in the internal phase G' exceeds G" at a lower frequency, compared to the behavior observed for the emulsions that do not contain agar in the internal phase (FIGS. 8a and 8b). This indicates that gelation of the internal droplets promotes solid-like behavior, as G' is a determinant of the elastic behavior whereas G" indicates viscous behavior (FIGS. 8a and 8b).

Water Contact Angle Measurements on Functional Membrane Surface

The location and morphology of dry domains embedded within polymeric membrane base would influence hydrophobicity of the membrane. The surface hydrophobicity was investigated through water contact angle (WCA) analysis on the templated membranes. Water contact angles (WCA) on surfaces of dry cast membranes were determined at room temperature and ambient relative humidity using goniometer (DataPhysics instruments, Germany). The membrane surfaces were 0.5-1 cm$^2$ wide. The membranes were characterized after solvent evaporation. A water droplet of 5 µl was deposited on the surface of each dry membrane and advancing contact angles were measured. All of the values reported are the average of four measurements taken at different locations of an individual membrane and have a maximum error of ±4°.

The functionalized polymer membranes which did not have agar gel in the internal phase were slightly less hydrophobic than sole SBS membrane. All contact angles measured for non-gel samples were stable and did not experience a significant variation over time. WCAs were measured around 75°-81°. FIGS. 6a and 6b show WCA measurement results for all samples within the range of 0.4-1.0% (w/v) nanoparticle concentration and 9-25% (v/v) internal volume fraction which had gelation of agar in the internal phase. FIG. 6a displays WCA's measured immediately after deposition of water droplets on the surface for all samples prepared with gel droplets. Immediately after water droplet deposition on a membrane surface, WCA measured were in between 68°-84°. However, some samples with gel domains displayed a changing contact angle due to the presence of higher internal phase and hence higher water absorption capacity by the gel phase. FIG. 6b demonstrates this particular group of samples which behaved different from the rest of the samples. For the membranes prepared with higher dispersed phase content (14 and 25% (v/v) and 0.7 and 1% (w/v) nanoparticle concentrations), the droplets were absorbed by the membrane 15 seconds after deposition on the surface, which reduced WCAs down to ~0°. The water uptake by the functional domains could be explained by strong water absorption capacity of the gel phase dispersed in the membrane formed via emulsion templating method. However, the fact that certain membranes display this behavior while the rest hold the water droplet on the surface with a steady WCA is intriguing. For the case of membrane samples prepared with 9% internal phase volume fraction, water could not be absorbed at any nanoparticle concentration by the membrane. Most probably, for these membranes, water content of the gel phase was at equilibrium and gel phase could not be swollen further. In addition, for the membranes prepared with 0.4% (w/v) of nanoparticle concentration, water could not be absorbed by the gel phase at any internal volume fraction condition (FIG. 6b). This could be explained by the fact that at low nanoparticle concentration condition, the droplet sizes are larger and hence evaporation of water in the internal phase is limited during drying step. This limits further swelling of the membrane. The lack of water absorption by these domains could also be explained by the fact that hydrophilic (salt or gel) domains were not at the top surface, and that they were covered by hydrophobic SBS. When the amount of hydrophilic domains was increased, the water drop was not stable on the top surface and decreased with time. This indicates that there are enough hydrophilic domains at the top surface which might also be connected causing the water drop to penetrate into the membrane. The membrane samples which demonstrated water absorption behavior contained closed packed functional domains, as was observed in FIGS. 4a and 4b.

Throughout this specification various indications have been given as to preferred and alternative embodiments of the invention. However, the foregoing detailed description is to be regarded as illustrative rather than limiting and the invention is not limited to any one of the provided embodiments. It should be understood that it is the appended claims, including all equivalents, are intended to define the spirit and scope of this invention.

The invention claimed is:

1. A controlled release composite membrane comprising:
    a hydrophobic styrene-butadiene-styrene block copolymer as a hydrophobic continuous medium, and
    Pickering emulsion droplets comprising at least one anti-icing agent surrounded and stabilized by a hydrophilic dispersed medium comprising hydrophobic silica nanoparticles.

2. The controlled release composite membrane of claim 1, wherein the at least one anti-icing agent is potassium formate.

3. The controlled release composite membrane of claim 1, wherein the hydrophilic dispersed medium comprises agar.

4. A process for preparing a controlled release composite membrane according to any of claim 1, 2 or 3 comprising:
    incorporating the at least one anti-icing agent into the hydrophobic styrene-butadiene-styrene block copolymer as hydrophobic continuous medium to form a mixture; and
    stabilizing the mixture with the hydrophobic silica nanoparticles using a Pickering emulsion templating method.

* * * * *